(12) United States Patent
Erzberger et al.

(10) Patent No.: US 9,554,804 B2
(45) Date of Patent: Jan. 31, 2017

(54) REDEPLOYABLE LEFT ATRIAL APPENDAGE OCCLUSION DEVICE

(71) Applicants: Gary S. Erzberger, Minneapolis, MN (US); Dara Chin, St. Paul, MN (US); Robert T. Sandgren, Lindstrom, MN (US); Michael Patrick Corcoran, Woodbury, MN (US)

(72) Inventors: Gary S. Erzberger, Minneapolis, MN (US); Dara Chin, St. Paul, MN (US); Robert T. Sandgren, Lindstrom, MN (US); Michael Patrick Corcoran, Woodbury, MN (US)

(73) Assignee: Cardia, Inc., Eagan, MN (US)

( * ) Notice: Subject to any disclaimer, the term of this patent is extended or adjusted under 35 U.S.C. 154(b) by 0 days.

(21) Appl. No.: 13/763,929

(22) Filed: Feb. 11, 2013

(65) Prior Publication Data

US 2013/0218193 A1      Aug. 22, 2013

Related U.S. Application Data

(63) Continuation-in-part of application No. 13/400,968, filed on Feb. 21, 2012.

(51) Int. Cl.
*A61B 17/12*      (2006.01)
*A61B 17/00*      (2006.01)

(52) U.S. Cl.
CPC ... *A61B 17/12122* (2013.01); *A61B 17/12172* (2013.01); *A61B 2017/00867* (2013.01); *A61B 2017/12054* (2013.01)

(58) Field of Classification Search
CPC .................. A61B 17/0057; A61B 2017/00575; A61B 2017/00579; A61B 2017/00584; A61B 2017/00588; A61B 2017/00592;A61B 2017/00597; A61B 17/12122; A61B 17/1214; A61B 17/12145; A61B 17/12022
USPC .......................................................... 606/213
See application file for complete search history.

(56) References Cited

U.S. PATENT DOCUMENTS

| | | |
|---|---|---|
| 4,007,743 A | 2/1977 | Blake |
| 6,689,150 B1 | 2/2004 | VanTassel et al. |
| 7,044,134 B2 | 5/2006 | Khairkhahan et al. |
| 7,582,104 B2 | 9/2009 | Corcoran et al. |
| 7,735,493 B2 | 6/2010 | van der Burg et al. |
| 7,905,901 B2 | 3/2011 | Corcoran et al. |
| 2003/0195555 A1 | 10/2003 | Khairkhahan et al. |
| 2005/0043759 A1 | 2/2005 | Chanduszko |
| 2005/0065547 A1 | 3/2005 | Marino et al. |
| 2008/0039929 A1 | 2/2008 | Davis et al. |
| 2009/0076541 A1 | 3/2009 | Chin et al. |
| 2009/0099647 A1 | 4/2009 | Glimsdale et al. |
| 2009/0171386 A1 | 7/2009 | Amplatz et al. |
| 2009/0292310 A1 | 11/2009 | Chin et al. |

(Continued)

OTHER PUBLICATIONS

Mar. 22, 2013 USPTO Office Action (U.S. Appl. No. 13/400,968).

(Continued)

*Primary Examiner* — Julian W Woo
*Assistant Examiner* — Shaun L David
(74) *Attorney, Agent, or Firm* — Beck Tysver Evans, PLLC

(57) ABSTRACT

A medical device implant for the left atrial appendage of a patient's heart to prevent strokes. The device includes a cap that overlies the opening of the LAA connected to a bulb in the LAA. Discontinuous segmented sails attached to the cap promote tissue growth over the device. The device maybe repositioned and redeployed during implantation.

1 Claim, 10 Drawing Sheets

(56) References Cited

U.S. PATENT DOCUMENTS

2011/0082495 A1    4/2011   Ruiz
2012/0065667 A1    3/2012   Javois et al.
2012/0172927 A1    7/2012   Campbell et al.

OTHER PUBLICATIONS

Apr. 23, 2013 PCT Search Report (Serial No. PCT/US13/027061).
Apr. 29, 2013 PCT Search Report (Serial No. PCT/US13/027065).
Nov. 22, 2013 USPTO Office Action (U.S. Appl. No. 13/400,968).
Feb. 6, 2014 PCT Preliminary Examination Report (Serial No. PCT/US13/027061).
Apr. 1, 2014 PCT Preliminary Examination Report (Serial No. PCT/US13/027065).
Jul. 2, 2014 USPTO Office Action (U.S. Appl. No. 13/400,968).
Nov. 2, 2015 USPTO Office Action (U.S. Appl. No. 13/400,968).
Jun. 16, 2015 USPTO Office Action (U.S. Appl. No. 13/400,968).

REDEPLOYABLE LEFT ATRIAL APPENDAGE OCCLUSION DEVICE

CROSS REFERENCE TO RELATED CASES

This application is a continuation-in-part of U.S. patent application Ser. No. 13/400,968 filed Feb. 21, 2012, entitled Left Atrial Appendage Occlusion Device.

FIELD OF THE INVENTION

The present invention related to implanted devices for use in occluding the left atrial appendage of patients. The device includes structures that permit the device to be easily retrieved and redeployed.

BACKGROUND OF THE INVENTION

It is widely understood that the occlusion of the left atrial appendage of the human heart will prevent strokes. The mechanism of action is that clots present within the left atrial appendage can become entrained into the general circulation and be transported to the brain where the clots can occlude arterial vessels causing an ischemic stroke.

Devices that have received significant clinical study include the "Plaato" device described in U.S. Pat. No. 6,152,144 among others, and the "Watchman" device described in U.S. Pat. No. 6,689,150 among others. Each of these clinically tested devices lies wholly within the left atrial appendage and includes a membrane that spans the opening or ostium of the left atrial appendage. The Watchman device is typically porous and in the Plaato device the membrane is impervious to the passage of blood. Additionally, the Watchman device uses a series of barbs or prongs which enter the tissue surrounding the ostium of the left atrial appendage to help secure the device during the acute phase of implant.

Although both of these devices appear to be successful, they each have shortcomings and drawbacks, which suggest that additional development is required for a widely acceptable and successful left atrial appendage device.

SUMMARY OF THE INVENTION

In contrast to the prior art clinical devices, the present invention provides a compliant cap that lies outside of the ostium of the LAA over the opening and is tethered or connected to an anchoring bulb positioned within the left atrial appendage. The overall device is highly compliant and conformable, and can accommodate a wide variety of sizes, shapes and volumes of left atrial appendage, which is desirable. The external cover cap is sufficiently pliant and conformable that is can flex to accommodate different contours of heart chamber near the left atrial appendage ostium. The cap includes multiple sail segments. These so-called "sails" are attached to the cap framework and they form a discontinuous but overlapping leaky structure. For example no individual sail structure spans the dimension of the ostium of the LAA. However, the multiple sails prevent clots from migrating but no attempt at blood filtration is made.

Overall the LAA device is made up from several wire loops that connect to independent posts. The cap framework includes single wire loops that overlap to form "petals". The bulb framework includes several wire loops that are gathered together and attached to each other at specified locations.

In general, each wire loop passes through two posts. The wire loops are loosely retained in the posts and the device exhibits many degrees of freedom and is highly flexible and compliant.

BRIEF DESCRIPTION OF THE DRAWINGS

Throughout the several figures like reference numerals indicate identical structure, and for this reason many reference numbers appear more than once, wherein.

DETAILED DESCRIPTION

Figure 1:
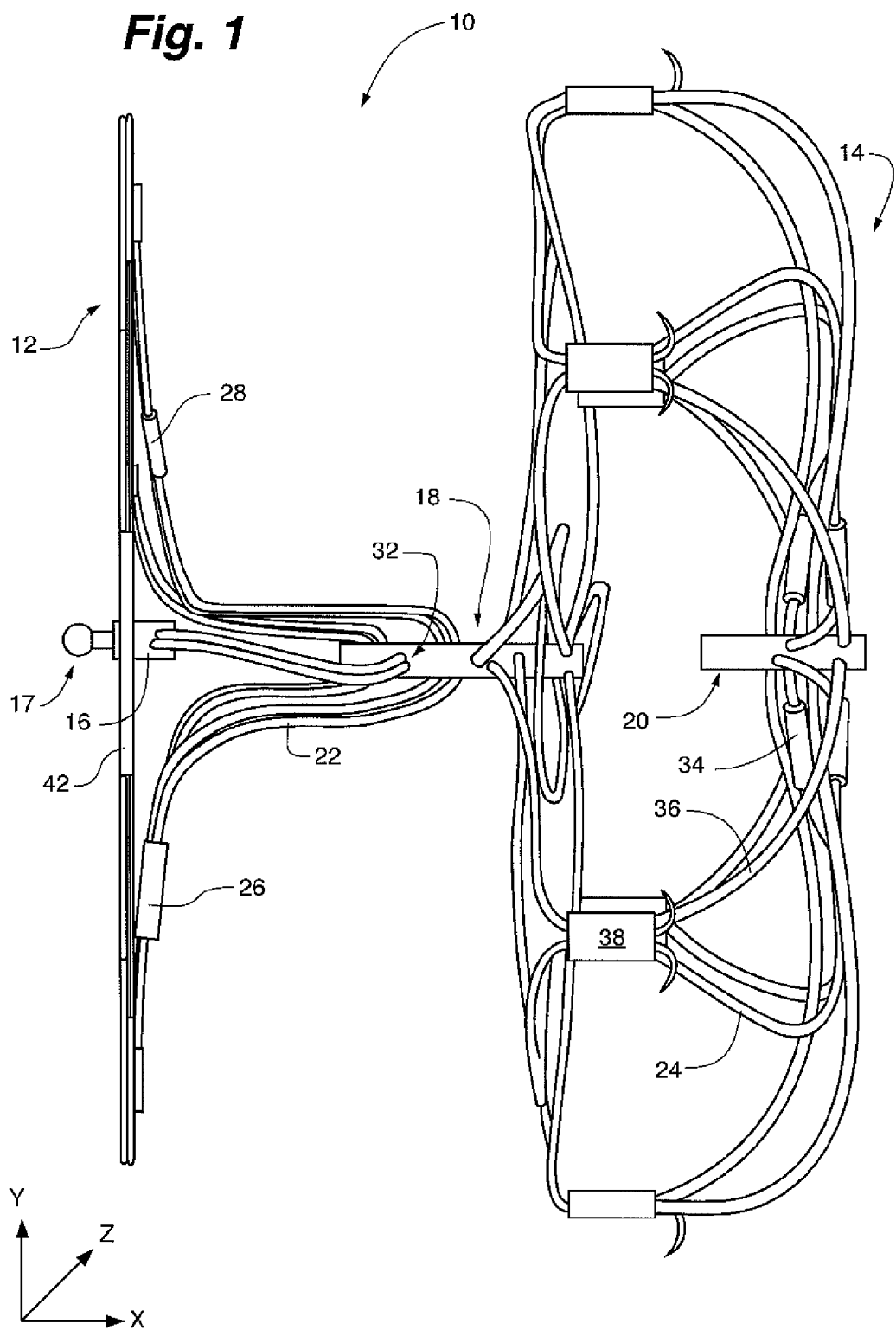
FIG. 1 is view of the LAA device in its un-deformed shape.

FIG. 1 shows the LAA device 10 seen from the side in its unstressed or un-deformed shape. The device includes a cap framework 12 and a bulb framework 14. As is common in medical devices the frameworks are manufactured primarily from Nitinol with a "shape memory" shape heat set during manufacture. The device assumes this shape in the un-deformed or unstressed condition. The interconnecting posts are made from titanium or any other compatible material. In general the wires are multi-stranded although monofilament wire may be substituted selectively. The use of multiple strands wire is preferred.

The cap framework is made up of a collection or set of wire loops, typified by the wire loop 22. Each wire loop for the cap framework is formed by a single Nitinol wire that passes though a hole in the proximal post 16, and a hole in the intermediate post 18. A crimp connector collars typified in the figure by crimp connector collar 26 or crimp connector collar 28 is used to collect the two ends of a single wire to form a wire loop indicated in the figure as wire loop 22. The holes in the posts are large enough to typically carry a single wire with some clearance. See for example the hole near reference numeral 32. All holes carry at least one wire. The wire fit in the holes is "loose" and the wire are free to move with respect to each other and importantly the wires do not transfer or share much force, through the posts, with each other in use. However, in manufacturing the hole shape is slightly altered by pressing, such that the wires may rotate but are restrained against translational motion through the hole. In essence the slight crushing of the posts preserves the overall shape of the device but compliance is preserved and enhanced. The wire loops are largely independent and decouple the cap framework 12 from the bulb framework 14. Typically each wire loop is heat set to form a loop that has a petal section in the Y-Z plane defined at reference numeral 30 and a linkage in the Y-X plane. That is each wire of the cap framework forms one of a number of independent petals that collectively make up the cap framework. Present but not well seen in this figure is a "sail" system 42 attached to elements of the cap framework 12. Also well seen in this figure is the connection feature 17 here shown as a ball shaped protuberance that can be captured by a delivery tool. The delivery tool seen at 19 in FIG. 5 can grasp the proximal post and thereby manipulate the device 10 in the delivery catheter 21 or in the heart chamber.

The bulb framework 14 is made up from a collection of wire loops as well. For example a wire loop 24 is made from a single wire that passes through the intermediate post 18 and the distal post 20, with the ends collected in a crimp connector collars seen at 34. In contrast to the cap framework, a companion coupler 38 connects loops such as 24 and its neighboring companion wire loop 36. Short barbs indicated by barb 40 are also placed at the couplers. The couplers connect two wire loops and permit forces to be shared by the two loops, for example loop 24 and loop 36 each influence each other while not influencing other wire loops.

Figure 2:
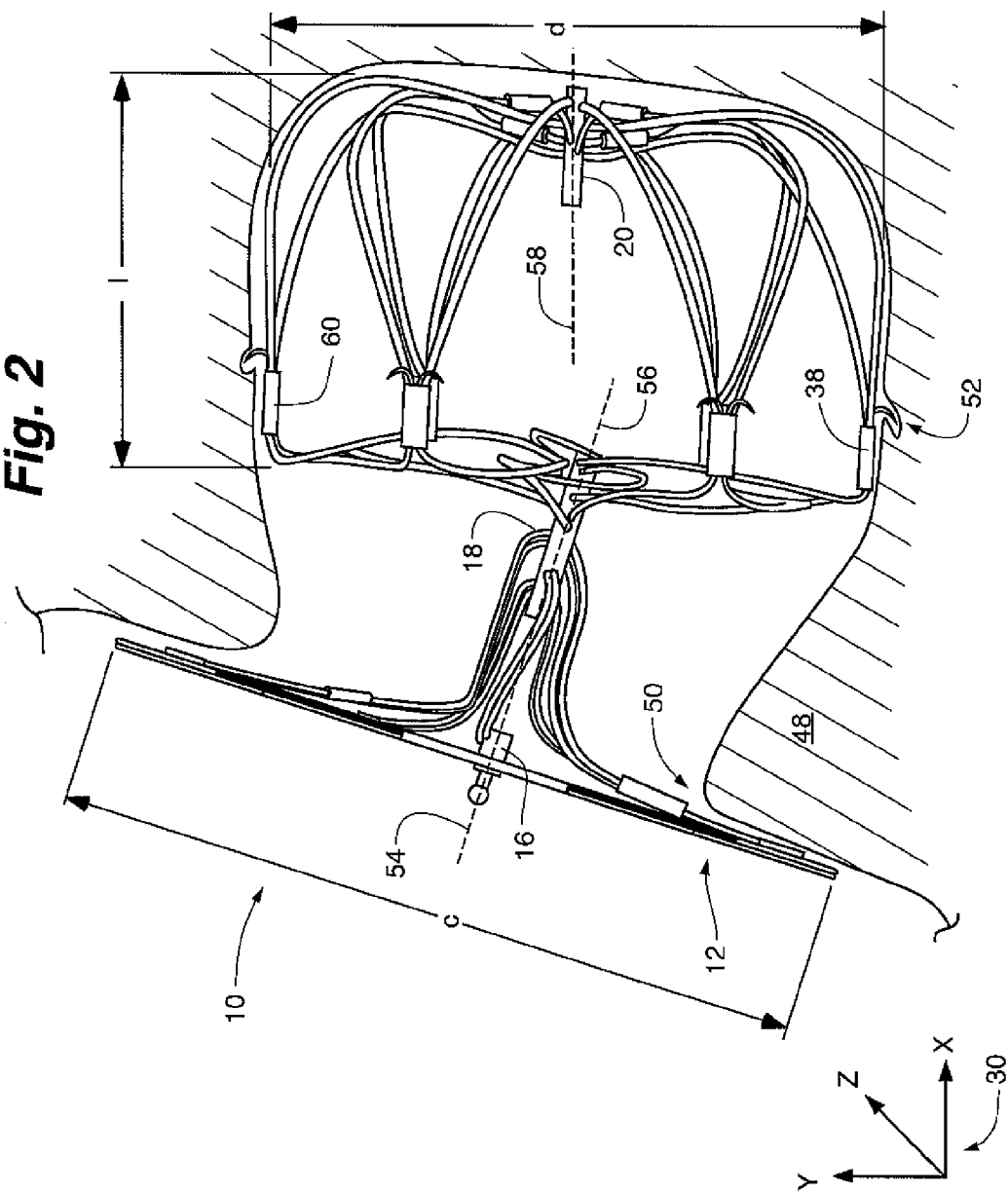
FIG. 2 is a view of the LAA device deformed into conformity with an LAA.

FIG. 2 shows the LAA device 10 in use in the left atrial appendage 48 of a patient. The petals of the cap framework 12 over-lie the generally annular opening ostium 50 of the LAA 48. In general the dimension "c" of the cap framework 12 is larger than the nominal diameter of the ostium 50. The bulb 14 is in the stressed state in this figure and the nominal diameter "d" of the bulb framework is reduced from the value of the corresponding dimension as seen in FIG. 1. The nominal length "l" of the device 10 in the stressed state is elongated from the unstressed state of FIG. 1. The LAA 48 supplies the forces required to impose these deformations and the reaction forces from the device will embed barbs such as barb 52 into the tissue proximate to the bulb 14. The figure also demonstrates that there is essentially no force applied to the cap framework by the deformation of the bulb 14. This independence results in substantial performance improvements and in general the heart chamber outside the ostium 50 dictates the shape or curvature of the cap framework and this tends to reduce the anchoring force required to retain the device 10 in the heart.

In FIG. 2 an axis is defined for each of the posts. Axis 54 for proximal post 16 is depicted in the figure. Axis 56 is defined for intermediate post 18 while axis 58 is defined for the distal post 20. Each axis is concentric and coaxial in the unstressed state of FIG. 1 but may align to any other direction under the deformation forces supplied by the native anatomy. The misalignment seen in FIG. 2 of the posts demonstrates the supple conformation of the device taken as a whole.

Figure 3:
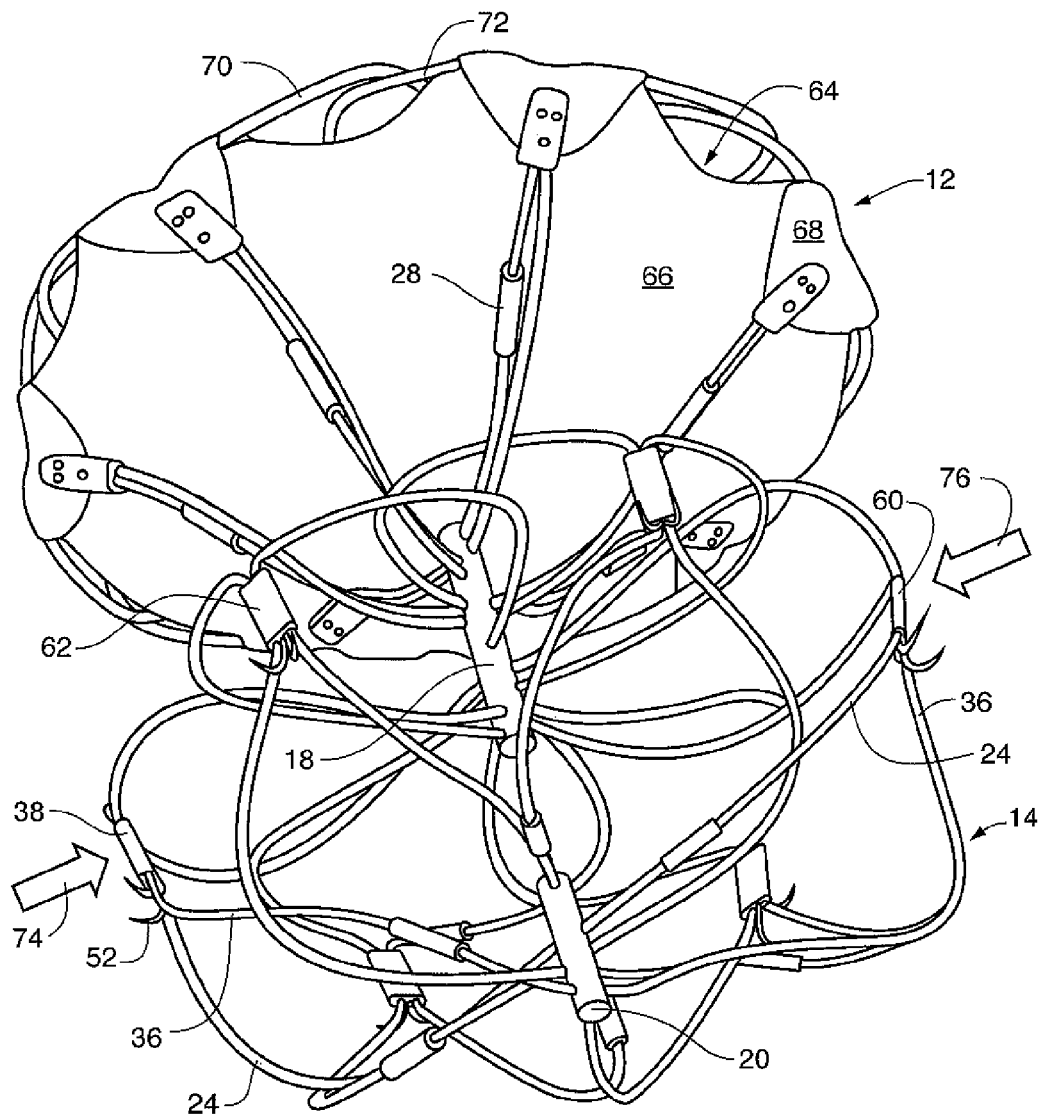
FIG. 3 is a perspective view of the device seen from the distal end.

FIG. 3 is a perspective view of the device 10 seen from the distal end and serves to show aspects and features better seen from this viewpoint. Here it is easier to discern the overlap of wire loop 70 and wire loop 72 as they form petals in the Y-Z plane. In this version of the device a single sail 66 is attached by fold over such as fold-over 68 to wire loop petals. The sail material is both flexible and "stretchy" when wet and little force is exerted on complimentary petals. For this reason it is possible for the cap framework to adopt non-circular forms and out of place curvatures in response to the native anatomy of the heart. The deep scallop cut 64 seen in the sail 66 prevents complete occlusion of the LAA. In general the sail material will be a polymer fabric of the type well known and used in implantable medical devices. Dacron and PVA fabrics are representative and not limiting examples of sail fabric.

The viewpoint of FIG. 3 also shows bulb framework wire loop 24 near coupler 38 and again across the device near coupler 60. The same is true for wire loop 36. By connecting these companion loops a force 74 is reacted to by forces at 76 and not elsewhere. That is the bulb does not deform regularly or evenly but rather opposing side are strongly coupled to each other but not to other wire loops. This unusual property results in a non-uniform but highly compliment device.

Figure 4:
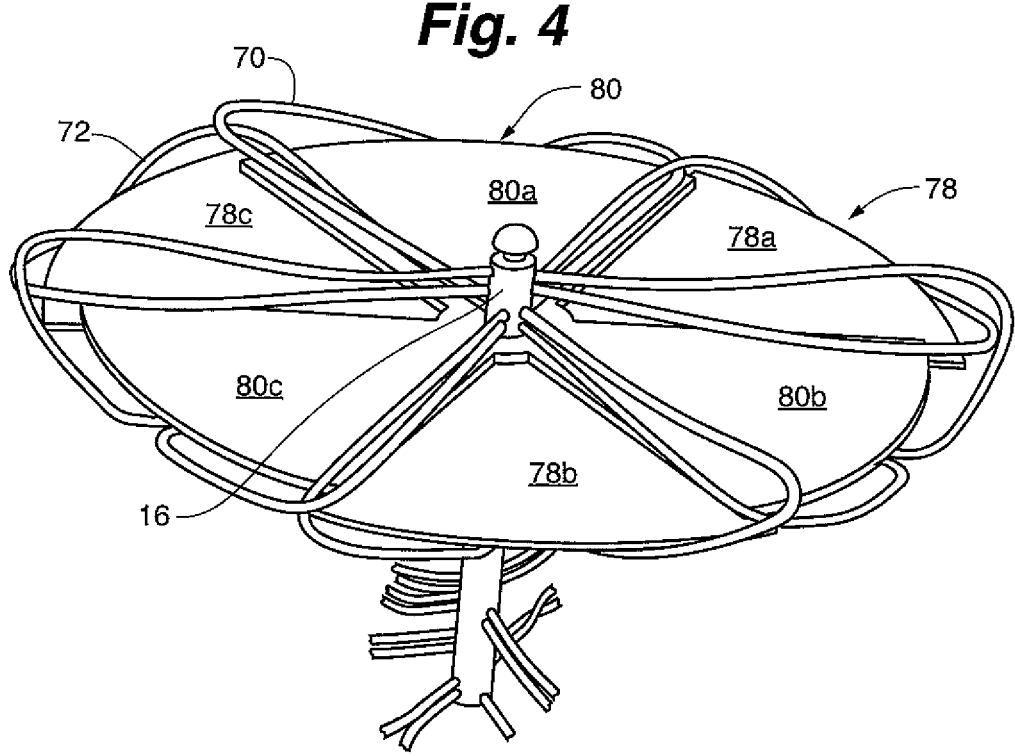
FIG. 4 is a perspective view of a portion of the device seen from the proximal end.

FIG. 4 shows a perspective view of the cap framework with an alternate sail configuration. Two separate sails 80 and 78 are seen in the figure with individually connected panel surfaces labeled 78a 78b and 78c for sail 78, while the panels of sail 80 are labeled 80a, 80b and 80c in the figure. These overlapping structures serve to promote tissue growth and permit independent motion of the petals such as those formed by wire loops 70 and 72. Blood flow but not clots will leak out and into the LAA b passing around the edges of the panels.

Figure 5:
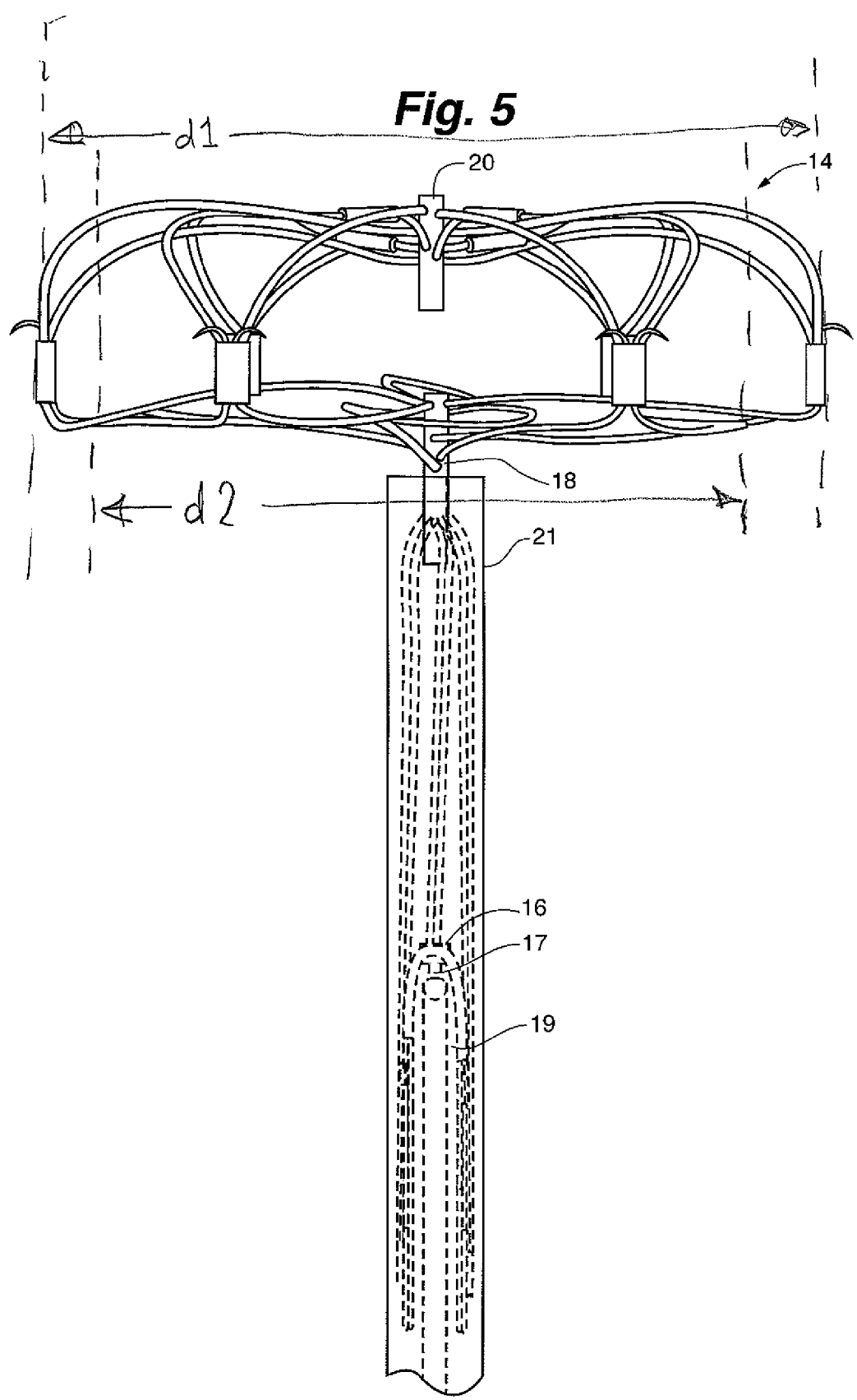
FIG. 5 is a view of the device partially deployed out of a delivery catheter.

FIG. 5 shows a deployment catheter in a somewhat schematic form. LAA devices are delivered to the LAA though a long delivery catheter 21 that enters the patient in the groin and passes though the septum into the left heart from the right heart. This pathway is well known and need not be described in detail. In the figure the distal bulb has been deployed out to the delivery catheter with the intermediate post 18 and proximal post 16 still partially in the catheter. The deployed shape and unconstrained shape of the bulb 14 reveals the independence of the shapes and decoupled nature of the device. The delivery tool 19 grasps the connection feature 19 to manipulate the device. The delivery tool 19 can push or pull the device 10 into or out of the delivery catheter 21. The compliance of the design facilitates deployment and recapture of the device 10.

Also seen in this figure is the nominal diameter of the device bulb framework 14 label d1 in the figure. As the framework is pulled into the delivery catheter 21 the bulb dimension moves form d1 to the smaller value d2 shown in the figure. This diameter reduction occurs over a very short amount of retraction. This feature causes the barbs 52 or hooks to retract out of tissue without tearing the tissue. This retraction is label in the figure with reference numeral 51.

Figure 6:
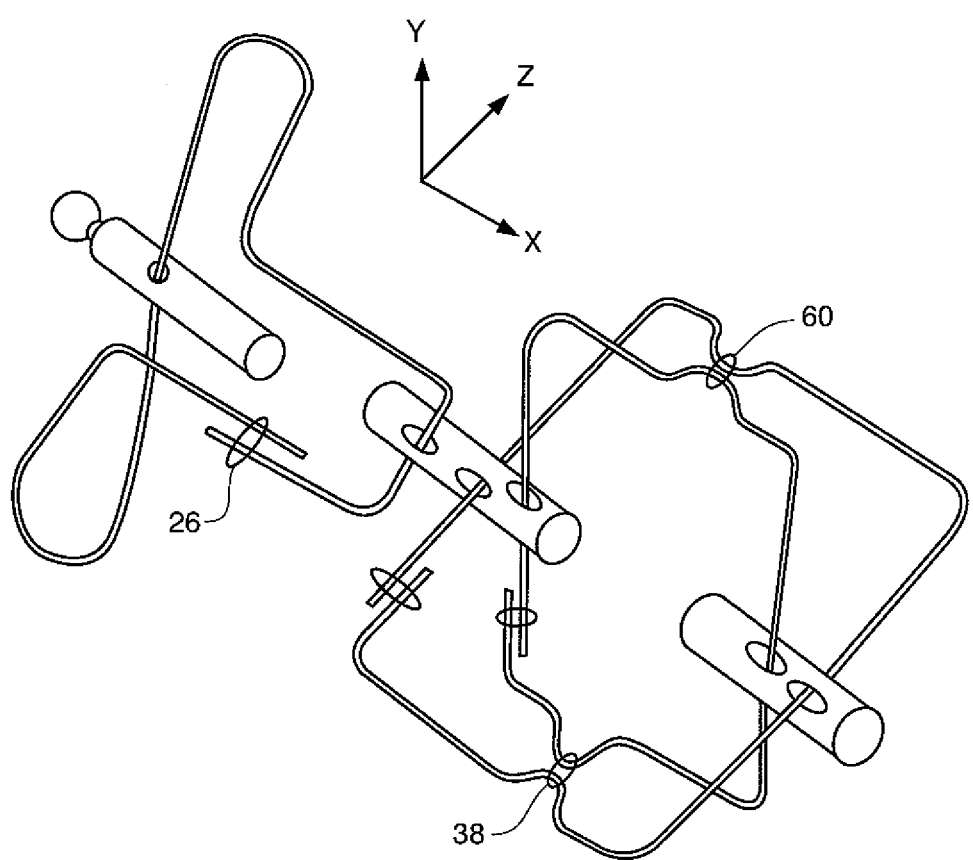
FIG. 6 is a schematic diagram in exaggerated scale to show the topology of the device.

FIG. 6 is a schematic diagram that is intended to display the topology of the device and as a consequence the scale of the post and wires have been exaggerated to more clearly display the interconnections between elements. For example a single wire 22 is passed though post 16 and heat formed to make two petals in the Y-Z plane, it then traverses the in the x direction to pass though the intermediate post 18. A crimp connector collars or weld seen at reference 26 connects the two ends of the wire. Two wire loops are seen in the bulb area. Wire 24 and 36 each pass though both the intermediate and distal posts. Crimp connections or the like are seen in the figure to close the loops. Exaggerated connections between the two wires are seen at 38 and 60. These couplers allow these two bulb wires to share or exchange force independently of the other bulb wires not shown in the figure to simplify the drawing.

Figure 7:
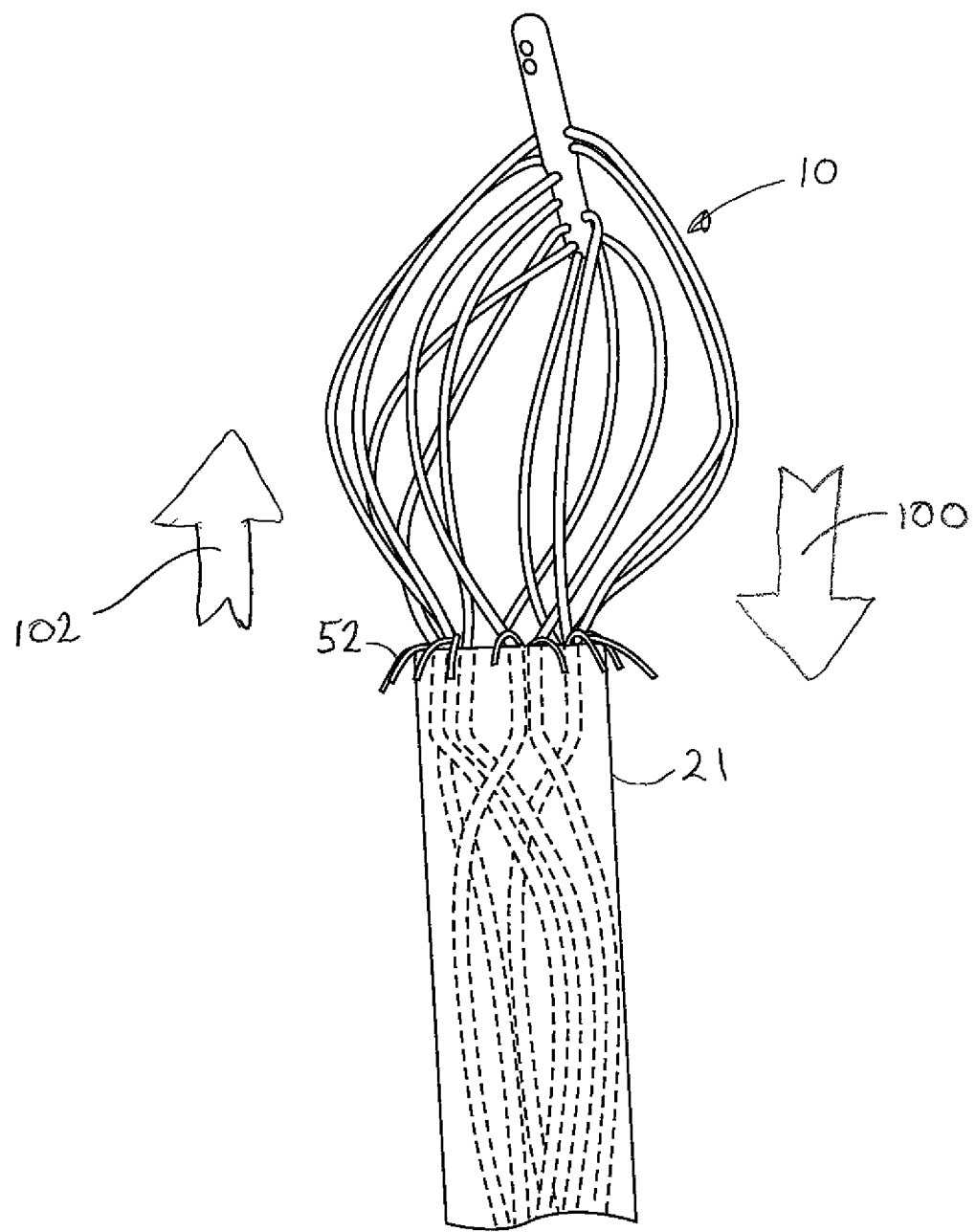
FIG. 7 is a view of the device being drawn into or emerging from a deployment sheath.

FIG. 7 is a view of the device 10 being drawn into indicated by motion arrow 100, or emerging from a deployment sheath 21 indicated in the figure by motion arrow 102. In the drawing the barbs or hooks typified by barb 52 are groomed by the catheter aperture into an untangled form. Each hooks moves neatly in to the open lumen of the catheter sheath 21.

Figure 8:
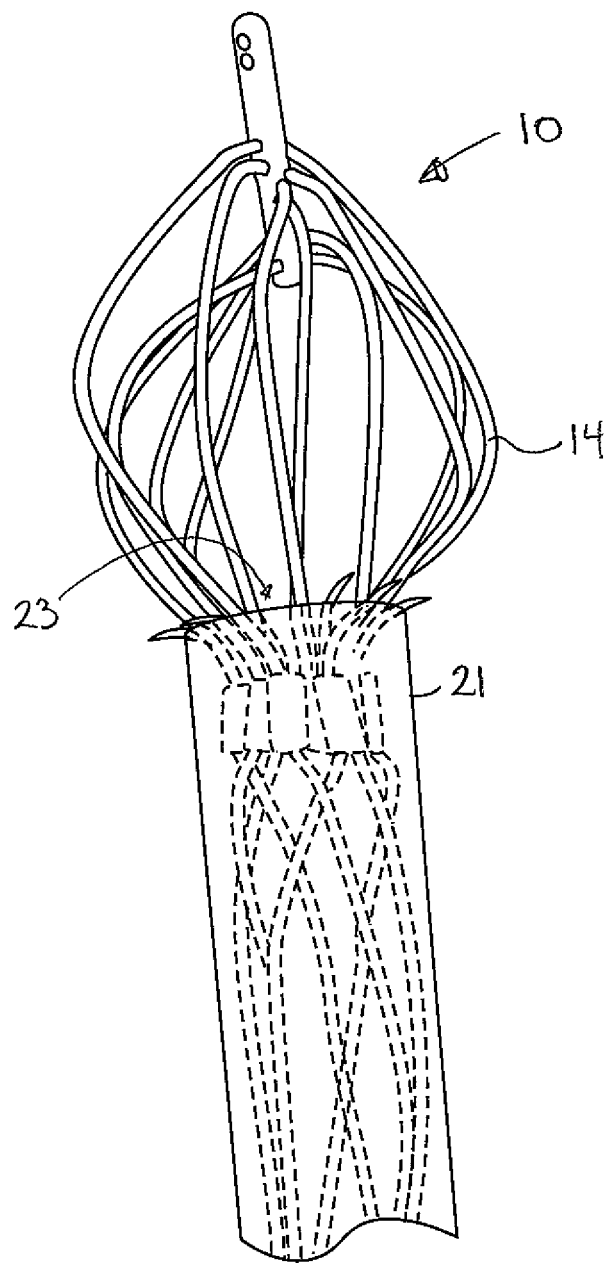
FIG. 8 is a partial view of the device in a deployment sheath.

FIG. 8 is a view of the bulb framework 14 of the device 10 being drawn into the deployment sheath 21. Here the barbs are facing the open ostium 23 of the sheath 21.

Figure 9:
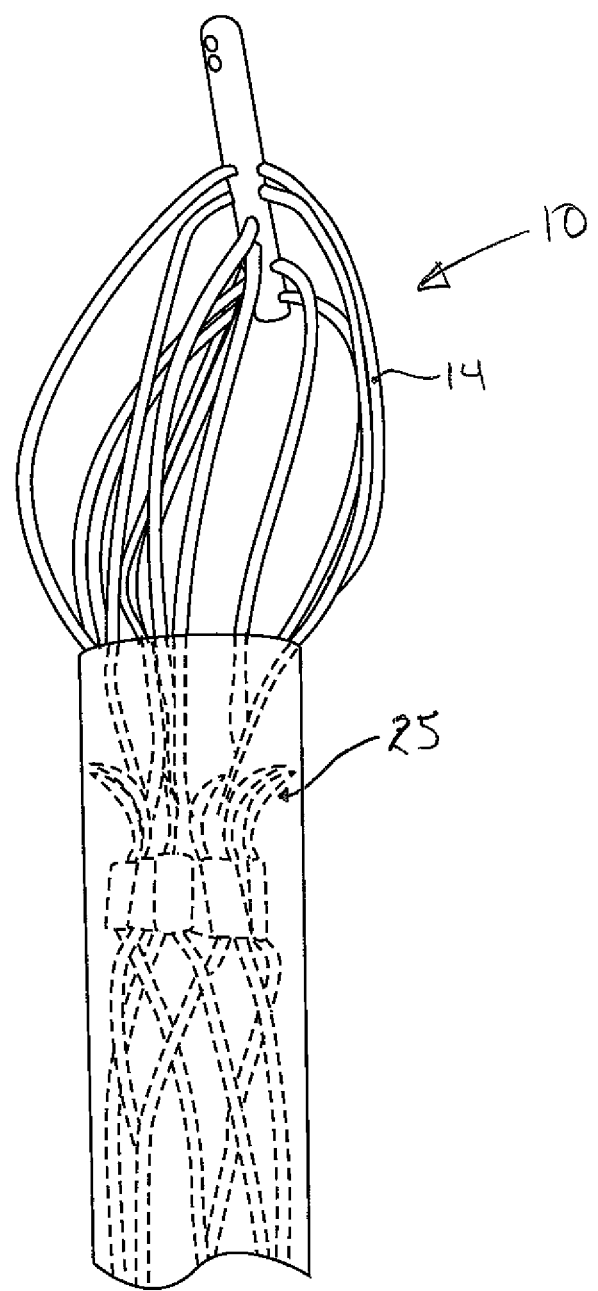
FIG. 9 is a partial view of the device in a deployment sheath.

FIG. 9 is a view of the bulb framework 14 of the device 10 being drawn into the deployment sheath 21. Here the barbs are withdrawn into the sheath 21 and they all point distally as seen at reference numeral 25.

Figure 10:
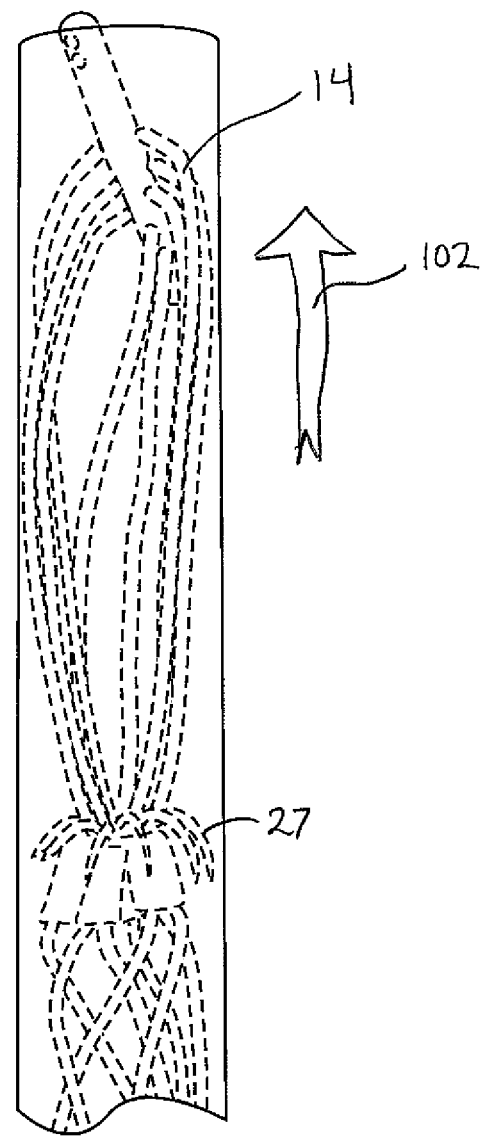
FIG. 10 is a partial view of the device being pushed with the hooks flipping over for deployment.

FIG. 10 is a view of the bulb framework being pushed out of the sheath 21. The hooks or barbs have flipped over and they now point toward the proximal end of the sheath 21. For example barb at location 27 now points in the "other direction" than at location 25 in FIG. 9. This "flipping of the hooks" allows the device to deployed and redeployed safely and retrieved back into the sheath quickly to achieve optimal positioning in the patient.

The barb members may be implemented as short pieces of multi-strand nitinol wire wound in the form of a cable. Each barb element will have a distal end which may have chisel point or other "pointy" configuration. Each barb element may have a proximal end trapped and crimped or welded to the framework. As a design alternative each barb element may be an extension of a loop wire. In either embodiment the distal tip is supported as a cantilever anchored on the frame.

What is claimed is:

1. A medical device to treat the left atrial appendage (LAA) of a patient, said LAA having an interior and having an ostium, said medical device delivered through a delivery catheter having a tubular delivery lumen, said medical device comprising:
   a. a cap framework, having an area greater than the area of the ostium of the LAA; said cap framework including,
      I. a single cylindrical proximal post having a set of orthogonal proximal post apertures and,
      II. a single cylindrical intermediate post having a set of orthogonal intermediate post apertures,
      III. a set of cap framework cable loops,
         each of said set of cable loops passing through one of said orthogonal proximal post apertures and passing through one of said orthogonal intermediate post apertures;
   b. a bulb framework, for tethering said cap framework from a location within said LAA; said bulb framework including,
      I. a single cylindrical distal post having a set of orthogonal distal post apertures;
      II. a set of bulb framework cable loops,
         each of said set of bulb framework cable loops passing through one of said orthogonal distal post apertures of said single cylindrical distal post and passing though one of said orthogonal intermediate post apertures,
         each of said bulb framework cable loops coupled to a companion bulb cable loop with a bulb cable loop coupler that captures each of said cable loops and hold them together in a parallel side by side relationship;
   c. a plurality of curved tissue penetrating barbs connected to said bulb cable loop coupler, each of said curved tissue penetrating barbs adapted to point proximally during bulb framework advancement out of said delivery lumen and to point distally upon bulb retraction into said delivery lumen by grooming interaction with said tubular delivery lumen; a segmented sail having multiple sail segments attached to said cap framework; each sail segment having an area smaller than the area of said ostium of said LAA.

* * * * *